United States Patent [19]

Trucks et al.

[11] 4,113,739
[45] Sep. 12, 1978

[54] PROCESS FOR PREPARATION OF (POLY)CYCLIC POLYETHERS

[75] Inventors: Roger O. Trucks; Edwin C. Steiner, both of Midland, Mich.

[73] Assignee: The Dow Chemical Company, Midland, Mich.

[21] Appl. No.: 437,425

[22] Filed: Jan. 28, 1974

[51] Int. Cl.$^2$ ............................................. C07D 493/10
[52] U.S. Cl. ................................. 260/338; 260/340.7; 260/340.9 R
[58] Field of Search .................. 260/338, 340.7, 340.9

[56] References Cited
U.S. PATENT DOCUMENTS

| | | | |
|---|---|---|---|
| 3,562,295 | 2/1971 | Pedersen | 260/338 |
| 3,687,978 | 8/1972 | Pedersen | 260/340.3 |
| 3,763,188 | 10/1973 | Krespan | 260/338 |

OTHER PUBLICATIONS

Fieser et al., Reagents for Organic Synthesis, pp. 911–917 (1967).

Primary Examiner—Norma S. Milestone
Attorney, Agent, or Firm—David H. Fifield

[57] ABSTRACT

In the preparation of (poly)cyclic polyethers by a cyclic Williamson synthesis, the improvement of contacting the reactants in a hindered ($C_4$–$C_{14}$) alkanol. For example, bis-chloroethyl ether and the disodium salt of tetraethylene glycol are contacted in t-butanol to produce the cyclic polyether

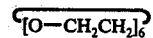

in high yields.

11 Claims, No Drawings

PROCESS FOR PREPARATION OF (POLY)CYCLIC POLYETHERS

BACKGROUND OF THE INVENTION

1. Field of the Invention

This invention pertains to the preparation of (poly)cyclic polyethers. Cyclic polyethers comprised of certain oxyalkylene units are known to selectively complex certain alkali and alkaline earth metal cations as well as other cationic species; C. J. Pedersen, U.S. Pat. Nos. 3,562,295 and 3,686,225.

2. Description of the Prior Art

Preparation of the cyclic tetramer of ethylene oxide by the cyclization of ethylene oxide over an organometallic catalyst, for example triethyl aluminum, ethyl zinc butoxide or diethyl magnesium, is taught by Stewart, et al. in British Specification No. 785,229. C. J. Pedersen in U.S. Pat. No. 3,687,978 teaches the preparation of macrocyclic polyethers by the reaction of vicinal aromatic diols with $\alpha,\omega$-dihalides of polyoxyalkylene materials and sodium hydroxide in 1-butanol solvent. Pedersen also describes the preparation of the cyclic oxyethylene hexamer by the autoelimination reaction of the $\alpha,\omega$-chlorohydrin of hexaethylene glycol in the presence of potassium t-butoxide in a 1,2-dimethoxy ethylene solvent in U.S. Pat. No. 3,562,295. The ethylene oxide cyclic hexamer is produced in a very low yield of 1.8%. Dale et al. describe a base catalyzed preparation in Chem. Comm. 670 (1971). There, glycols and glycol ditosylates are condensed with potassium t-butoxide in benzene in about 15–35% yields.

SUMMARY OF THE INVENTION

The improvement discovered in the cyclic Williamson synthesis improves yields and consists of carrying out the synthesis in a tertiary or otherwise hindered lower alkanol or a mixture of such alkanols. Suitable hindered alkanols are those represented by the formula:

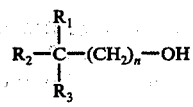

where $n$ is 0 or 1 and $R_1$, $R_2$ and $R_3$ are independently alkyl groups of one to about four carbon atoms. For example, 2-methyl-2-propanol (t-butanol), 3-ethyl-3-pentanol, 4-propyl-4-heptanol, 2-methyl-2-butanol (t-amyl alcohol), 2,2-dimethyl-1-propanol (neopentyl alcohol), 2-methyl-2-pentanol, 2,4-dimethyl-2-pentanol, 3-methyl-3-pentanol, 3-ethyl-2-methyl-3-pentanol, 2,3-dimethyl-3-pentanol, 3-methyl-3-heptanol, 4-ethyl-4-heptanol and the like may suitably be employed. t-Butanol, t-amyl alcohol and neopentyl alcohol are the solvents of choice with t-butanol being especially preferred.

The chosen alkanol or alkanol mixture may be used alone or as a mixture with one or more compatible aprotic solvents such as benzene. If such a mixture is employed, the alkanol component(s) should comprise greater than about 40% of the mixture by volume.

DETAILED DESCRIPTION OF THE INVENTION

We have noted that some of the polyether products may be toxic if their vapors are inhaled and possibly from skin contact. The reactions and subsequent handling of products should therefore be carried out with due precaution for safety.

The process by which the hydroxyl substituent of an organic substrate and the halide substituent of the same organic substrate or of another organic substrate undergo condensation in the presence of a strong base, such as sodium hydroxide, with the subsequent formation of an ether linkage between the substrate points of prior hydroxyl and halide functionality is commonly referred to as a Williamson synthesis. Similarly, the condensation reaction between an organic halide and an alkali metal alkoxide with consequent ether linkage between the substrates may also be referred to as a Williamson synthesis. As used herein, the term "Williamson synthesis" refers to either of the above-described reactions. The term "cyclic Williamson synthesis" refers to the use of such Williamson synthesis to produce cyclic products.

Such reactions may be represented by the equations:

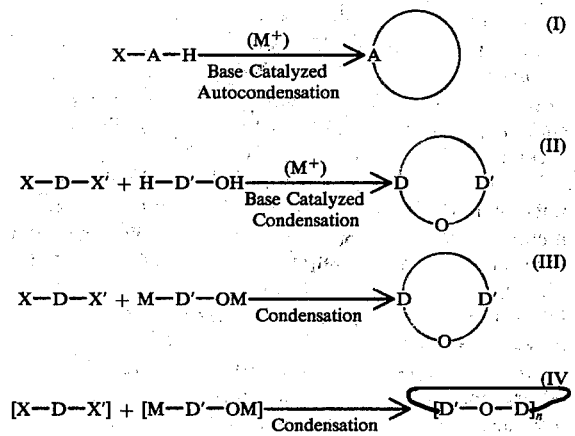

wherein X and X' are independently chlorine, bromine or iodine; M+ is an alkali metal ion (lithium, sodium, potassium rubidium or cesium) from the metal, metal hydroxide or metal alkoxide; $n$ is an integer from 1 to about 4; A is a polyoxyalkylene chain of about 4 to about 10 lower oxyalkylene units; D is a lower alkylene or (poly)oxyalkylene substrate represented by the formula $-Z+OX+_q$ where Z is a lower alkylene unit and q is an integer from 0 to about 7; and D' is a lower polyoxyalkylene chain represented by the formula $+OZ+_m$ where m is an integer from 2 to about 9, and the sum of $m$ and $q$ is about 9 or less. As used herein, the terms "lower alkylene," "lower oxyalkylene" and "lower (poly)oxyalkylene" signify moieties, the alkylene portion of which comprises an ethylene or propylene group which may bear from one to four or six, respectively, $C_1$-$C_3$ alkyl substituents.

Process Conditions

The cyclic Williamson syntheses are conveniently carried out in a closed vessel under an inert atmosphere, for example nitrogen, helium, argon or the like, to prevent oxidation of the reactants by air. Sufficient pressure should be maintained to prevent the possible influx of air to the reactor vessel. Pressure is otherwise not a critical factor.

Reaction temperatures vary depending on the route chosen for preparation of the polyether product. Suitable temperatures will be about room temperature to about 200° C. The optimum temperature for a given set of reactants may be readily determined by one skilled in the art.

The strong alkali metal base employed in Reactions I and II as a source of alkali metal ions is suitably any alkali metal, alkali metal hydroxide or alkali metal alkoxide of one of the chosen solvents. Suitable bases therefore include lithium, sodium, and potassium metals and their hydroxides, sodium t-butoxide, potassium neopentyl alkoxide, lithium t-amyl alkoxide, etc.

The relative proportion of reactants employed will conveniently approximate chemical equivalence. For Reaction I, about one mole of strong base is suitably employed for each mole of halohydrin reactant. In Reaction II, two moles of strong base are suitably employed for each mole of $\alpha,\omega$-diol reactant. Equimolar amounts of dialkali metal salt and dihalide are reacted in Reactions III and IV.

The amount of solvent employed is chosen so that the mixture is handled conveniently, for example, about 0.5 to about 2 moles of combined reactants per liter of solvent is convenient in most instances.

The desired (poly)cyclic polyether products are conveniently recovered by extracting the reaction mixture with a suitable organic solvent. Inorganic by-products such as alkali metal halides will remain in the aqueous layer as will any excess inorganic base.

In some instances, the (poly)cyclic polyether products will be recovered as complexes with the alkali metal halides. The pure polyether may be separated from complexed polyether or the complex broken by the selection of a suitable solvent, e.g., hot benzene. Other solvents suitable for these purposes may be determined by standard procedures of the art.

Under certain conditions, the production of polyethers where $n$ is greater than 1 will be favored. In such instances, chiefly where $m$ is 1 or 2 and $q$ is 0 or 1, the product will be composed of polyethers where $n$ is predominantly 2 and 3. These congeneric telomer products may be separated by conventional techniques, e.g., by fractional distillation.

Reactants

The reactants will obviously vary depending on the structure desired in the cyclic product.

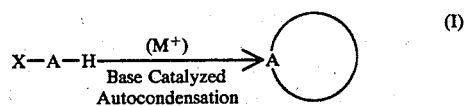
(I)

In Reaction I, the $\alpha,\omega$-halohydrin to be cyclized by autocondensing may be represented by the formula HAX wherein X is chlorine, bromine or iodine and A is comprised of lower oxyalkylene units represented by the formula

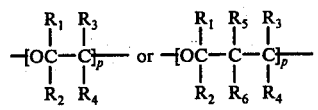

wherein $p$ is preferably an integer from about 4 to about 10; $R_1$, $R_2$, $R_3$, $R_4$, $R_5$ and $R_6$ are independently hydrogen or alkyl of one to about three carbon atoms, or $R_5$ and $R_6$ may join to form oxetane, dioxolane or dioxane heterocycles containing the quaternary carbon as a member of such a heterocycle.

In Reactions II, III and IV condensations the reactants may be represented by the formulas XDX', HD'OH and MD'OM wherein X and X' are independently chlorine, bromine or iodine and M is an alkali metal (lithium, sodium, potassium, rubidium or cesium). The difunctional substrate D is a group represented by the formula $-Z+OZ+_q$ wherein Z may be the same substituted lower alkylene units as in A and $q$ is preferably an integer from 0 to about 7. D' is a difunctional substrate represented by the formula $+OZ+_m$ and $m$ is preferably an integer from 2 to about 9, the sum of $m$ and $q$ being about 9 or less.

In preferred embodiments of Reaction I, one of polyoxyethylene- and polyoxypropylene-$\alpha,\omega$-chlorohydrins of about 4 to about 10 oxyalkylene units is cyclized in t-butanol.

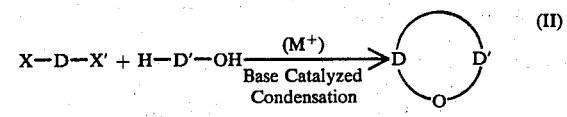
(II)

In preferred embodiments of Reaction II, a 3,3-bis(halomethyl)oxetane is contacted with one of the compounds represented by the formulas H$+$OCH$_2$CH$_2$$]$OH,

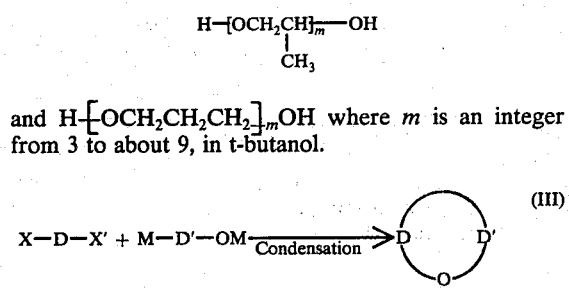

and H$+$OCH$_2$CH$_2$CH$_2$$]_m$OH where $m$ is an integer from 3 to about 9, in t-butanol.

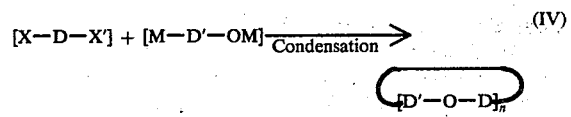
(III)

In preferred embodiments of Reaction III, the corresponding dialkali metal salts of the above-mentioned glycols are contacted with a 3,3-bis(halomethyl)oxetane in t-butanol.

The utilization of two relatively short-length reactants in Reaction III will result in Reaction IV taking place with a mixture of polyether products.

$$[X-D-X'] + [M-D'-OM] \xrightarrow{\text{Condensation}} \quad (IV)$$

$$\bigl(D'-O-D\bigr)_n$$

The reactants are selected so that the (poly)cyclic polyether products will be composed of the desired (poly)-oxyalkylene substrates. For Reaction I, for example, where a product of the formula $$\bigl(OCH_2CH_2\bigr)_5$$

is desired, the corresponding $\alpha,\omega$-chlorohydrin of pentaethylene glycol would be chosen as the starting material to be contacted with the strong alkali metal base. For Reaction II, where a product of the formula $$\overbrace{-(O-CH_2CH_2)_3-OCH_2CH\underbrace{\phantom{xx}}_{CH_3}}$$

is desired, for example, triethylene glycol could be contacted with 1,2-dihalo-propane or, alternatively, ethylene glycol could be contacted with the compound represented by the formula $$XCH_2CH_2OCH_2CHOCH_2CH_2X$$
$$\phantom{XCH_2CH_2OCH_2}|\phantom{OCH_2CH_2X}$$
$$\phantom{XCH_2CH_2OCH_2}CH_3$$

to produce the same results. Similarly, the compound of the formula $$\begin{array}{c} O \\ CH_2 \diagup \diagdown CH_2 \\ ClCH_2-C-CH_2Cl \end{array}$$

may be contacted with tetraethylene glycol to produce the polycyclic polyether represented by the formula $$\overbrace{-(OCH_2CH_2)_4-O-CH_2-\underset{CH_2\diagdown O \diagup CH_2}{C}-CH_2-}$$

The dialkali metal salts of (poly)oxyalkylene $\alpha,\omega$-diols corresponding to the (poly)alkylene glycols of Reaction II are employed in Reactions III and IV with a suitably chosen (poly)oxyalkylene or alkylene $\alpha,\omega$-dihalide. For instance, the dipotassium salt of tetraethylene glycol may be contacted with bis-chloroethyl ether to form a polyether of the formula $$\overbrace{-(OCH_2CH_2)_6-}$$

When the disodium salt of diethylene glycol is contacted with 3,3-bis(bromomethyl)oxetane, a mixture of polycyclic polyethers is produced represented by the formula $$\left[\overbrace{-(OCH_2CH_2)_2-O-CH_2-\underset{CH_2\diagdown O \diagup CH_2}{C}-CH_2-}\right]_n$$

where $n$ is primarily 2 and 3.

It may be observed from these illustrations that the nature of the final polyether product is determined by the choice of suitable reactants.

SPECIFIC EMBODIMENTS OF THE INVENTION

In the following examples, the reactant(s) are contacted (in the presence of a strong base in Reactions I and II) in a flask or stainless steel bomb under an inert atmosphere, normally nitrogen. The products were analyzed by mass spectroscopy, nuclear magnetic resonance (NMR) spectroscopy, vapor phase chromatography (VPC) and/or elemental analysis. Yields are based on the amount of designated reactant charged.

EXAMPLE 1 t-Butanol Solvent, Base Catalyzed

A three-necked flask equipped with condenser, magnetic stirrer and nitrogen inlet was evacuated and then flushed with nitrogen three times. To the nitrogen-filled flask, 17.2 g. of t-butanol, 1.6 g. (14.3 mmoles) of potassium t-butoxide and 1.43 g. (7.3 mmoles) of tetraethylene glycol were added and thoroughly mixed. Thereafter, 1.06 g. (7.4 mmoles) of bis-chloroethyl ether was added to the mixture with stirring and the resulting mixture was heated at about 100° C. for approximately 3 hours. Excess solvent was stripped off on a rotary evaporator. The resudue was dissolved in methylene chloride and washed with water; the wash water was extracted with 3 portions of methylene chloride; all organic fractions were combined, stripped of solvent and flashed distilled to give about a 32% yield of product by VPC (based on tetraethylene glycol). This product was identified as the cyclic oxyethylene hexamer by gas liquid chromatography with tetraethylene glycol monomethyl ether as an internal standard.

EXAMPLE 2 t-Butanol-Benzene Solvent

In a similar manner, to a mixture of 11.6 g. of t-butanol and 9.5 g. benzene, under a nitrogen atmosphere, were added 1.36 g (13.7 mmoles) of the disodium salt of triethylene glycol and 1 g. (14 mmoles) of bis-choroethyl ether. The mixture was heated at about 100° C. for approximately 4 hours, aliquot analyses showed little further reaction after about 2 hours, and the resulting mixture was then treated in the conventional manner and about a 45% yield of product (by VPC based on disodium salt reactant) was recovered and identified as cyclic oxyethylene pentamer.

EXAMPLE 3

Benzene Solvent

In a like manner, 0.74 g. of the disodium salt of triethylene glycol and 0.54 g. of bis-chloroethyl ether were mixed in 18.8 g. of benzene alone and heated at about 100° C. for about 3 hours. VPC analysis showed about a 2% yield of the cyclic oxyethylene pentamer (based on disodium salt reactant).

The superiority of the hindered alkanol in this process is readily apparent from these cyclic Williamson syntheses with and without t-butanol.

EXAMPLE 4

Dioxane Product

The reactant 2,2-dimethyl-5,5-bis(bromomethyl)-1,3-dioxane was prepared by contacting 2,2-bis(-bromomethyl) 1,3-propane diol with an excess of acetone in the presence of a catalytic amount of hydrochloric acid. Water produced in the reaction was removed with anhydrous calcium chloride and any residual acid was neutralized with sodium carbonate, the mixture filtered and the filtrate evaporated to dryness. The residue was extracted with carbon tetrachloride, filtered and the filtrate evaporated to give the desired 2,2-dimethyl-5,5-bis(bromomethyl)-b 1,3-dioxane reactant.

About 330 mmoles of the prepared dioxane reactant was then contacted under a nitrogen atmosphere with the disodium salt of tetraethylene glycol (prepared by contacting about 310 mmoles of tetraethylene glycol and 590 mmoles of clean sodium metal) in t-butanol for about 6 hours at about 150° C. The solvent was then removed under vacuum to yield a solid containing the desired product and NaBr. The product was extracted from the solid sodium bromide residue with hot benzene; the benzene was evaporated under vacuum and the residual oil distilled to give 63 g. (a 64% yield based on the sodium) of a product corresponding to the formula:

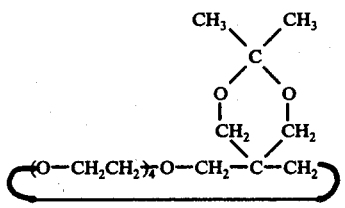

EXAMPLE 5

Oxetane Cyclic Tetramer

In a similar manner 150 g. (1 mole) of triethylene glycol and 46 g. (2 moles) of sodium metal were contacted under a nitrogen atmosphere in 1500 ml. of t-butanol at about 55°–60° C. to produce the disodium salt of triethylene glycol. The mixture was cooled to about 45° C. and 244 g. (1 mole) of 3,3-bis(bromomethyl)oxetane were added and the temperature raised to about 50°–60° C. for about 15 minutes and then heated at about 80°–85° C. for about 6 hours with sodium bromide precipitating. The mixture was cooled to about 25°–30° C. and filtered. The precipitated salt was washed with hot benzene, the washings collected and concentrated by boiling off benzene and added to the original filtrate from which t-butanol had been removed by heating.

The combined filtrates were then distilled under vacuum to give 77.1 g. of a product (33% yield based on triethylene glycol) corresponding to the formula:

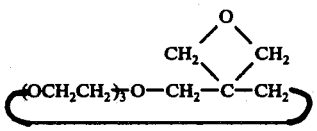

EXAMPLE 6

Oxetane Cyclic Hexamer

In the manner of Example 5, 217 g. (0.914 mole) of pentaethylene glycol and 42 g. (1.825 moles) sodium were contacted in 1500 ml. of t-butanol to produce the disodium salt which was reacted with 222 g. (0.912 mole) of 3,3-bis(bromo-methyl)oxetane. After extraction and distillation, 191.9 g. (95-98% pure by VPC) of liquid product (about 65% yield based on the oxetane reactant) was recovered corresponding to the formula:

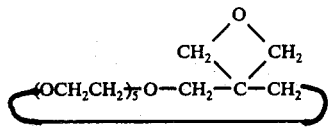

EXAMPLE 7

Neopentyl Alcohol Solvent, Dioxolane Product

A reactant represented by the formula

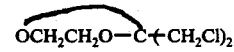

is prepared by contacting, in about equimolar amounts, ethylene glycol and bis(chloromethyl) ketone in the presence of a catalytic amount of concentrated hydrochloric acid, neutralizing the acid, removing the resultant salt by aqueous washings and decantations and finally drying the desired product over anhydrous calcium chloride. A mole of this reactant (2,2-bis(-chloromethyl-1,3-dioxolane) is then contacted in an argon atmosphere with a mixture of about a mole of heptapropylene glycol and about 2 moles of the sodium hydroxide in a solvent of neopentyl alcohol. The mixture is refluxed to allow the reaction to occur and the resulting product is recovered and purified as described in Example 5. The product is a compound represented by the formula:

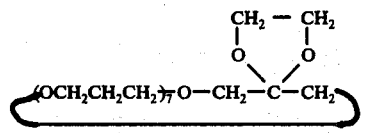

The above compounds are useful for forming complexes with the cations of numerous ionic salts (e.g., sodium, potassium, etc.) and those with oxetane and dioxane functionality are also useful as reactive intermediates since on contact with acid or basic aqueous solutions, respectively, dihydroxy functional cyclic ethers are produced which may be copolymerized with diisocyanates, dicarboxylic acids, etc. to form polyurethane or polyester resins and the like.

We claim:

1. In the process of preparing (poly)cyclic polyethers by:
    (a) autocondensing a polyoxyalkylene α,ω-halohydrin in the presence of a strong alkali metal base;
    (b) condensing, by contacting, a (poly)oxyalkylene α,ω-diol with an alkylene or a (poly)oxyalkylene α,ω-dihalide in the presence of a strong alkali metal base; or
    (c) condensing, by contacting, the dialkali metal salt of a (poly)oxyalkylene α,ω-diol with an alkylene or a (poly)oxyalkylene α,ω-dihalide;
the improvement of effecting the preparation in a hindered alkanol or hindered alkanol mixture the alkanol(s) having from 4 to about 14 carbon atoms.

2. The process of claim 1 wherein the hindered alkanol employed is t-butanol, t-amyl alcohol or neopentyl alcohol.

3. The process of claim 2 wherein the hindered alkanol is t-butanol.

4. The process of claim 1 wherein a polyoxyalkylene α,ω-halohydrin comprising from about 4 to about 10 lower oxyalkylene units is cyclized by autocondensation.

5. The process of claim 4 wherein the lower oxyalkylene units are oxyethylene or oxypropylene units.

6. The process of claim 5 wherein a polyoxyethylene- or polyoxypropylene-α,ω-chlorohydrin is employed and the hindered alkanol is t-butanol.

7. The process of claim 1 wherein a (poly)oxyalkylene α,ω-diol or its dialkali metal salt comprising from 2 to about 9 lower oxyalkylene units is contacted with an alkylene or (poly)oxyalkylene α,ω-dihalide.

8. The process of claim 7 wherein the alkylene or (poly)oxyalkylene α,ω-dihalide is selected from the group consisting of: ethylene α,ω-dihalides; propylene α,ω-dihalides; 3,3-bis(halomethyl)oxetanes; 2,2-bis(halomethyl)-1,3-dioxolanes; and 5,5-bis(halomethyl)-1,3-dioxanes.

9. The process of claim 8 wherein 3,3-bis(bromomethyl)oxetane is employed as the alkylene α,ω-dihalide.

10. The process of claim 9 wherein an α,ω-disodium salt of (poly)ethylene or (poly)propylene glycol of 2 to about 9 oxyethylene or oxypropylene units is employed as the (poly)oxyalkylene α,ω-diol dialkali metal salt and the hindered alkanol is t-butanol.

11. The process of claim 3 wherein the polycyclic polyether is prepared by contacting the disodium salt of triethylene glycol with 3,3-bis(bromomethyl)oxetane.

* * * * *

UNITED STATES PATENT AND TRADEMARK OFFICE
CERTIFICATE OF CORRECTION

PATENT NO. : 4,113,739
DATED : September 12, 1978
INVENTOR(S) : Roger O. Trucks and Edwin C. Steiner It is certified that error appears in the above-identified patent and that said Letters Patent are hereby corrected as shown below:

Column 2, line 43: "potassium rubidium or cesium)" should read --potassium, rubidium or cesium)--.

Column 2, line 48: "$-Z\{OX\}_q$" should read -- $-Z\{OZ\}_q$ --.

Column 4, lines 28 and 29: "$H\{OCH_2CH_2\}OH,$" should read -- $H\{OCH_2CH_2\}_m OH,$ --.

Column 6, line 18: "resudue" should read --residue--.

Column 6, line 68: "dimethyl-5,5-bis(bromomethyl)-b 1,3-dioxane" should read --dimethyl-5,5-bis(bromomethyl)-1,3-dioxane--.

Signed and Sealed this

Nineteenth Day of December 1978

[SEAL]

Attest:

RUTH C. MASON
Attesting Officer

DONALD W. BANNER
Commissioner of Patents and Trademarks